(12) United States Patent
Meystre et al.

(10) Patent No.: US 10,290,370 B2
(45) Date of Patent: May 14, 2019

(54) SYSTEMS AND METHODS FOR EXTRACTING SPECIFIED DATA FROM NARRATIVE TEXT

(71) Applicant: University of Utah Research Foundation, Salt Lake City, UT (US)

(72) Inventors: Stéphane Michael Meystre, Sandy, UT (US); Óscar Ferrández Escamez, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 936 days.

(21) Appl. No.: 14/285,343

(22) Filed: May 22, 2014

(65) Prior Publication Data

US 2014/0350965 A1    Nov. 27, 2014

Related U.S. Application Data

(60) Provisional application No. 61/826,867, filed on May 23, 2013.

(51) Int. Cl.
    *G16H 15/00*       (2018.01)
    *G16H 10/60*       (2018.01)
    *G06F 19/00*       (2018.01)

(52) U.S. Cl.
    CPC ............. *G16H 15/00* (2018.01); *G06F 19/00* (2013.01); *G16H 10/60* (2018.01)

(58) Field of Classification Search
    CPC ............. G06F 17/2785; G06F 19/3418; G06F 19/3481; G06F 17/271; G16H 15/00; G16H 10/60

(Continued)

(56) References Cited

U.S. PATENT DOCUMENTS

2007/0073704 A1*   3/2007   Bowden ............ G06F 17/30867
2008/0294459 A1*  11/2008   Angell ................. G06F 19/328
                                                              705/2

(Continued)

FOREIGN PATENT DOCUMENTS

WO    WO-2009105088 A2 *   8/2009   ........... G06F 19/325

OTHER PUBLICATIONS

Zhou, Li, "Using Medical Text Extraction, Reasoning and Mapping System (MTERMS) to Process Medication Information in Outpatient Clinical Notes," AMIA Annu Symp Proc. 2011; 2011: 1639-1648 (Year: 2011).*

(Continued)

*Primary Examiner* — Elaine Gort
*Assistant Examiner* — John P Go
(74) *Attorney, Agent, or Firm* — Workman Nydegger (57) ABSTRACT

Embodiments are directed to extracting specified data items from narrative text. In one scenario, a computer system accesses narrative textual information which includes data items that are to be identified and extracted. The computer system identifies specified data items in the narrative textual information that are to be extracted from the narrative textual information. The computer system then filters the identified data items to remove false positive identifications. The false positive filtering includes classifying the identified data items as specified data items, so that classified data items are identified as true positive items that are to be extracted from the narrative textual information. The computer system further extracts, from the narrative textual information, those filtered data items that were classified as being true positive items.

20 Claims, 4 Drawing Sheets

(58) Field of Classification Search
 USPC .................................................. 705/2, 3, 4
 See application file for complete search history.

(56) References Cited

U.S. PATENT DOCUMENTS

| | | | | |
|---|---|---|---|---|
| 2010/0223214 | A1* | 9/2010 | Kirpal ............... | G06F 17/30917 706/12 |
| 2011/0004588 | A1* | 1/2011 | Leitersdorf ....... | G06F 17/30864 707/711 |
| 2011/0071851 | A1* | 3/2011 | Alden .................. | G06F 19/327 705/3 |
| 2012/0116812 | A1* | 5/2012 | Boone ................. | G06F 17/2725 705/3 |
| 2012/0212337 | A1* | 8/2012 | Montyne ................ | G10L 15/26 340/501 |
| 2012/0221347 | A1* | 8/2012 | Reiner ................... | G06Q 10/00 705/2 |

OTHER PUBLICATIONS

Meystre, Stephane, "Comparing Natural Language Processing Tools to Extract Medical Problems from Narrative Text," AMIA Annu Symp Proc. 2005; 2005: 525-529 (Year: 2005).*
International Search Report and Written Opinion for PCT/US14/39316 dated Sep. 24, 2014.

* cited by examiner

SYSTEMS AND METHODS FOR EXTRACTING SPECIFIED DATA FROM NARRATIVE TEXT

CROSS-REFERENCE TO RELATED APPLICATIONS

This application claims priority to and the benefit of U.S. Provisional Application No. 61/826,867, entitled "SYSTEMS AND METHODS FOR EXTRACTING SPECIFIED DATA FROM NARRATIVE TEXT", which was filed on May 23, 2013, and which is incorporated by reference in its entirety herein.

BACKGROUND

Medical errors (and specifically, medication errors) are recognized as an important cause of injuries and death. Many could be prevented. These errors cause an estimated 44,000 to 98,000 deaths and 1,000,000 injuries every year in the U.S. Among these preventable deaths in the U.S., about 7,000 can be associated with medication errors, which is more than the number attributable to work-related injuries. Medication errors also cause 400,000 preventable injuries each year in hospitals, as well as 800,000 injuries in long-term care settings, and 530,000 injuries among Medicare recipients in outpatient clinics. The preventable injuries caused by medication errors in hospitals alone result in around $3.5 billion in additional medical costs.

Computerized physician order-entry (CPOE) systems may be able reduce this risk of medical or medication errors. These systems, however, only reduce errors when they provide decision support, including the detection of interactions between medications, and medication contraindications related to allergies, laboratory testing results, or diseases. These systems typically rely on structured and coded information in the electronic health record (e.g., entries in a problem list), but a substantial proportion of this information is only mentioned in narrative clinical text documents. Newly implemented "meaningful use" rules establish requirements such as maintaining a list of problems, and a list of medication allergies in the electronic health record (EHR) of 80% of inpatients. Besides decision support and lists of problems or allergies, summarizing the patient record, reporting, billing, and secondary uses of clinical data (e.g., clinical research) all require structured and coded information.

BRIEF SUMMARY

Embodiments described herein are directed to extracting specified data items from narrative text. In one embodiment, a computer system accesses narrative textual information which includes data items that are to be identified and extracted. The computer system identifies specified data items in the narrative textual information that are to be extracted from the narrative textual information. The identifying includes at least one of the following: performing a dictionary-based search, performing a pattern-based search and implementing machine learning to identify the data items that are to be extracted. The computer system then filters the identified data items to remove false positive identifications. The false positive filtering includes classifying the identified data items as specified data items, so that classified data items are identified as true positive items that are to be extracted from the narrative textual information. The computer system further extracts, from the narrative textual information, those filtered data items that were classified as being true positive items.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

Embodiments described herein are directed to extracting specified data items from narrative text. In one embodiment, a computer system accesses narrative textual information which includes data items that are to be identified and extracted. The computer system identifies specified data items in the narrative textual information that are to be extracted from the narrative textual information. The identifying includes at least one of the following: performing a dictionary-based search, performing a pattern-based search and implementing machine learning to identify the data items that are to be extracted. The computer system then filters the identified data items to remove false positive identifications. The false positive filtering includes classifying the identified data items as specified data items, so that classified data items are identified as true positive items that are to be extracted from the narrative textual information. The computer system further extracts, from the narrative textual information, those filtered data items that were classified as being true positive items.

The following discussion now refers to a number of methods and method acts that may be performed. It should be noted, that although the method acts may be discussed in a certain order or illustrated in a flow chart as occurring in a particular order, no particular ordering is necessarily required unless specifically stated, or required because an act is dependent on another act being completed prior to the act being performed.

Embodiments described herein may implement various types of computing systems. These computing systems are now increasingly taking a wide variety of forms. Computing systems may, for example, be handheld devices, appliances, laptop computers, desktop computers, mainframes, distributed computing systems, or even devices that have not conventionally been considered a computing system. In this description and in the claims, the term "computing system" is defined broadly as including any device or system (or combination thereof) that includes at least one physical and tangible processor, and a physical and tangible memory capable of having thereon computer-executable instructions that may be executed by the processor. A computing system may be distributed over a network environment and may include multiple constituent computing systems.

Computing systems, as used herein, typically include at least one processing unit and memory. The memory may be physical system memory, which may be volatile, non-volatile, or some combination of the two. The term "memory" may also be used herein to refer to non-volatile mass storage such as physical storage media. If the computing system is distributed, the processing, memory and/or storage capability may be distributed as well.

As used herein, the term "executable module" or "executable component" can refer to software objects, routings, or methods that may be executed on the computing system. The different components, modules, engines, and services described herein may be implemented as objects or processes that execute on the computing system (e.g., as separate threads).

In the description that follows, embodiments are described with reference to acts that are performed by one or more computing systems. If such acts are implemented in software, one or more processors of the associated computing system that performs the act direct the operation of the computing system in response to having executed computer-executable instructions. For example, such computer-executable instructions may be embodied on one or more computer-readable media that form a computer program product. An example of such an operation involves the manipulation of data. The computer-executable instructions (and the manipulated data) may be stored in the memory of the computing system. Computing system may also contain communication channels that allow the computing system to communicate with other message processors over a wired or wireless network.

Embodiments described herein may comprise or utilize a special-purpose or general-purpose computer system that includes computer hardware, such as, for example, one or more processors and system memory, as discussed in greater detail below. The system memory may be included within the overall memory. The system memory may also be referred to as "main memory", and includes memory locations that are addressable by the at least one processing unit over a memory bus in which case the address location is asserted on the memory bus itself. System memory has been traditionally volatile, but the principles described herein also apply in circumstances in which the system memory is partially, or even fully, non-volatile.

Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical hardware storage media that store computer-executable instructions and/or data structures. Physical hardware storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the principles described herein may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

Still further, system architectures described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

Embodiments described herein generally relate to extracting specified data items from text documents. These data items may include medical problems (such as diagnoses), allergies, treatments, or other types of data items. These text documents may include narrative text, structured, form-based text or other types of text, especially that found in electronic health records (EHRs).

Figure 1:
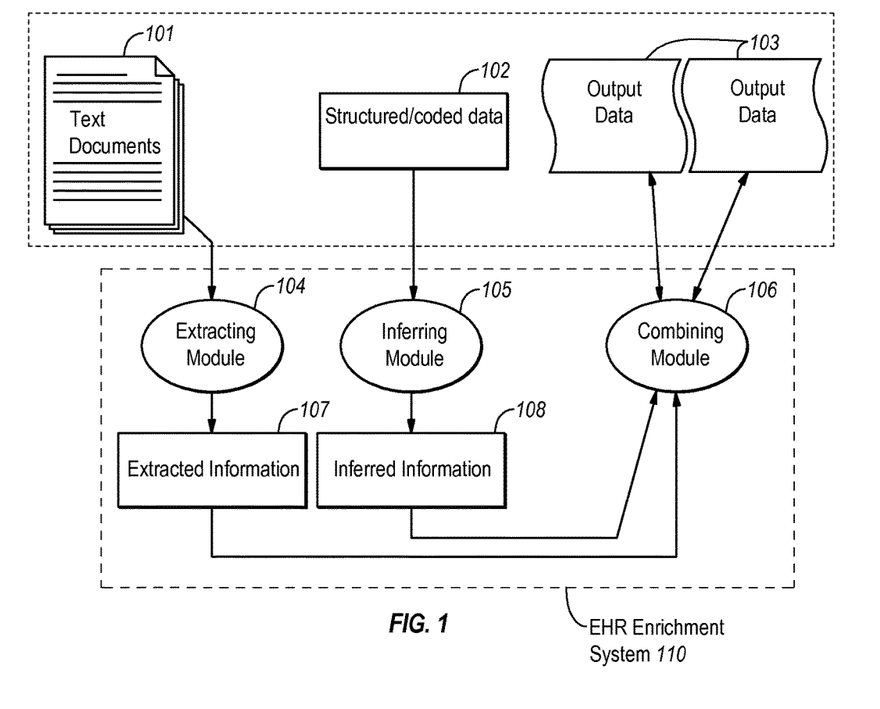
FIG. 1 illustrates a computer architecture in which embodiments described herein may operate including extracting specified data items from narrative text.

In one embodiment, an EHR enrichment system 110 may be implemented, as shown in FIG. 1. The EHR enrichment system may also use data mining and rules to infer possible medical problems and allergies (or other specified data) from existing structured clinical information in the EHR. The EHR enrichment system may further combine all this extracted and inferred information, and analyze the existing lists to prevent duplicates, highlight conflicts or possible errors, and notify users of where these lists or other inferred or extracted information came from. The EHR enrichment system 110 also indicates how the information was extracted or inferred. For instance, the information combining module 106 may note where the extracted information 107 and inferred information 108 were extracted and inferred, respectively.

Embodiments of the EHR enrichment system 110 are designed to support and help EHR or other types of records to create and maintain complete lists of a patient's medical problems, allergies, etc. As such, at least in some embodiments, the EHR enrichment system may assist in achieving "meaningful use" core objectives including the following: maintain up-to-date problem lists, and maintain active medication allergy lists. The EHR enrichment system 110 ensures that the medical problems and allergies a patient suffers from, and the medications the patient is taking, are clearly known by their healthcare providers. Moreover, the EHR enrichment system 110 ensures that this information is available for decision support and quality improvement, thereby improving the health care the patient will receive.

Still further, at least in some embodiments, the EHR enrichment system 110 assists healthcare providers in maintaining complete and timely lists of problems and allergies, providing them with an efficient overview of a patient, and further helping healthcare organizations attain meaningful use requirements. The EHR enrichment system may be used in inpatient and/or outpatient settings, in hospitals and/or private practices, increasing the efficiency of busy healthcare providers by saving time. The EHR enrichment system may further aid healthcare organizations in demonstrating "meaningful use" and obtaining Centers for Medicare & Medicaid Services incentive payments. Moreover, the EHR enrichment system may include an extended output that uses a modular design, allowing for utilization of each module and accumulated data to be offered as products. The EHR enrichment system may thus be applied to support efficient health care systems by extracting medical problems and allergies (or other information) from narrative or structured text documents (e.g. using the extracting module 104). The inferring module 105 may infer medical problems and allergies or other information from existing structured clinical information, or may access previously (manually entered) information in electronic lists.

The EHR enrichment system 110 may further be configured to apply Natural Language Processing (NLP) to automatically enrich lists of medical problems and allergies. It may further use NLP in real-time to support clinical care, and may also apply a stepwise hybrid approach for high accuracy information extraction. Natural language processing methods have previously been investigated to extract structured data from narrative text, with accuracy sometimes rivaling humans. However, most recent NLP research in the biomedical domain has focused on biomedical text (i.e. scientific publications), while clinical text has received less interest. Clinical text is often ungrammatical and "telegraphic" in style, rich in ambiguous abbreviations, and sometimes structured with templates or "text tables".

As mentioned above and as depicted in the conceptual model of FIG. 1, the EHR enrichment system 110 provides decision support systems with structured and coded information 102 about medical problems, allergies and other information. The EHR enrichment system may be configured to automatically extract medical problems, allergies and other types of information in real-time from narrative or other text documents 101 in the EHR or from another source, discovering possible medical problems, diagnoses, treatments, allergies or other information by mining existing structured clinical information in the EHR, and finally combining all this extracted information in to a data output 103 such as a dynamic list.

In one embodiment, a reference standard is created for training and testing the EHR enrichment system 110. This reference standard may include a random sample of de-identified clinical narrative documents (e.g. 101) with problems and allergies (or other specified data) annotated by domain experts. The total number of documents may be based on power calculations, and may ensure sufficient precision for proper measurement. The clinical documents may be selected from the EHR of patients in a study population. The clinical documents may be accessed and then automatically de-identified according to Heath Insurance Portability and Accountability Act (HIPAA) Safe Harbor rules. The reference standard may consist of documents with "annotations", the latter being structured information (e.g., type of data) with extents of the text. The annotation schema (i.e., a detailed list of information to annotate) may include medical concepts (e.g. problems, allergies, or other specified data), and modifiers (e.g. subject, temporality, negation, certainty).

Embodiments of the EHR enrichment system may thus automatically extract medical problems and allergies (or other specified data) in real-time from text documents including clinical narrative documents. Some embodiments may include the following design parameters: high accuracy (i.e. a focus is placed on high sensitivity, with good positive predictive value), and very fast performance (real-time and scalable). To meet these parameters, the information extraction system may implement a stepwise hybrid approach to maximize sensitivity first, and then filter out false positives to enhance positive predictive value. The information extraction system may also use fast methods and be optimized for speed. Such systems may be built on an enterprise-grade framework. This robust framework offers flexible and powerful scalability capabilities that include massive parallelization.

Figure 2:
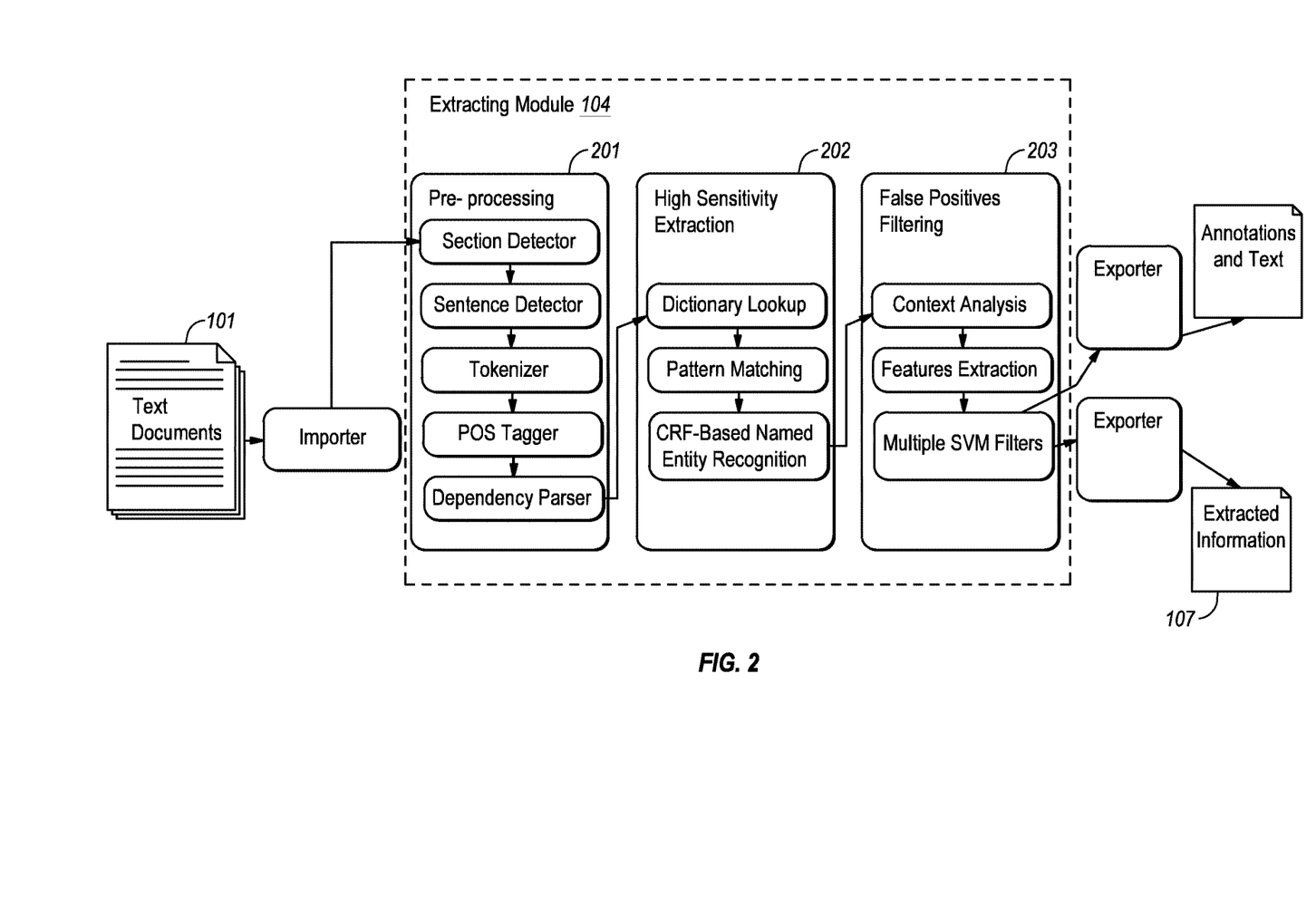
FIG. 2 illustrates an alternative computer architecture in which embodiments described herein may operate including extracting specified data items from narrative text.

The information extraction module 104 may include any number of different components for performing desired functionality. In some embodiments, as shown in FIG. 2, three main components may be used: a text pre-processing component 201, a high-sensitivity extraction component 202, and a false positives filtering component 203. The pre-processing component 201 may start by detecting and classifying clinical text sections (at least in some cases) based on machine learning classifiers. This may then be followed by sentence detection, in which the text is segmented into sentences, followed by tokenization, which splits the text into tokens such as words, numbers, symbols, and punctuation. The pre-processing component 201 may then implement part-of-speech (POS) tagging as well as dependency parsing. The dependency parser allows for fast processing, analyzing the syntactic dependencies of a sentence in very short timeframe. It should be noted that the pre-processing may include any one or more of the above components, or may include entirely different components, depending on the implementation.

The high-sensitivity extraction component 202 focuses on the extraction of possible medical problems, allergies or other information that might be of interest to a medical professional or staff member (provided to the user as extracted information 107), aiming at as high sensitivity as possible, even if numerous false positives are also detected. In some embodiments, the high-sensitivity extraction component 202 detects problems and allergies (or other specified data) with a dictionary lookup module. This dictionary lookup module may implement public or proprietary full-text search and indexing platforms, and may add extensions to known platforms. Pattern matching may implement regular expressions to detect specific strings of characters that denote problems or allergies (or other specified data), adding concepts that could have been missed by the dictionary lookup. Finally, a machine learning-based module may use Conditional Random Fields (CRF) to further enhance the sensitivity of the extraction. As with the pre-processing module, it should be noted that any or all of the above components may be implemented in the high-sensitivity extraction module 202. Alternatively, entirely different components may be used if so configured. This is also true for the false positives filtering component 203.

The false positives filtering component 203 classifies each "candidate" problem or allergy (or other specified data) from the high-sensitivity extraction component as a true positive or a false positive, and filters out the latter. It first analyses the local context of the extracted problems and allergies (or other specified data) by looking for expressions that indicate the negation or temporality of the concepts, or whether the patient or someone else is their subject. This functionality may be based on various dependency parse trees and/or lists of keywords. Different features used for the classification task are then extracted. The classifiers may be implemented as binary Support Vector Machines. For instance, one classifier may be implemented for medical problems, and another one for allergies (or still another for another specified data type). Using the features extracted previously, the Support Vector Machines classify each problem or each allergy as a true positive (i.e., a true problem or allergy), or as a false positive.

In the last processing step, the data 107 is exported in one or more different formats. For example, the data may be exported in a format that can be used to visualize the clinical narratives with highlighted problems and allergies (or other specified data) for quality control, while another format may be used to store the extracted information back into the EHR. These concepts will be described further below with regard to computing architecture 300 of FIG. 3 and method 400 of FIG. 4.

Figure 3:
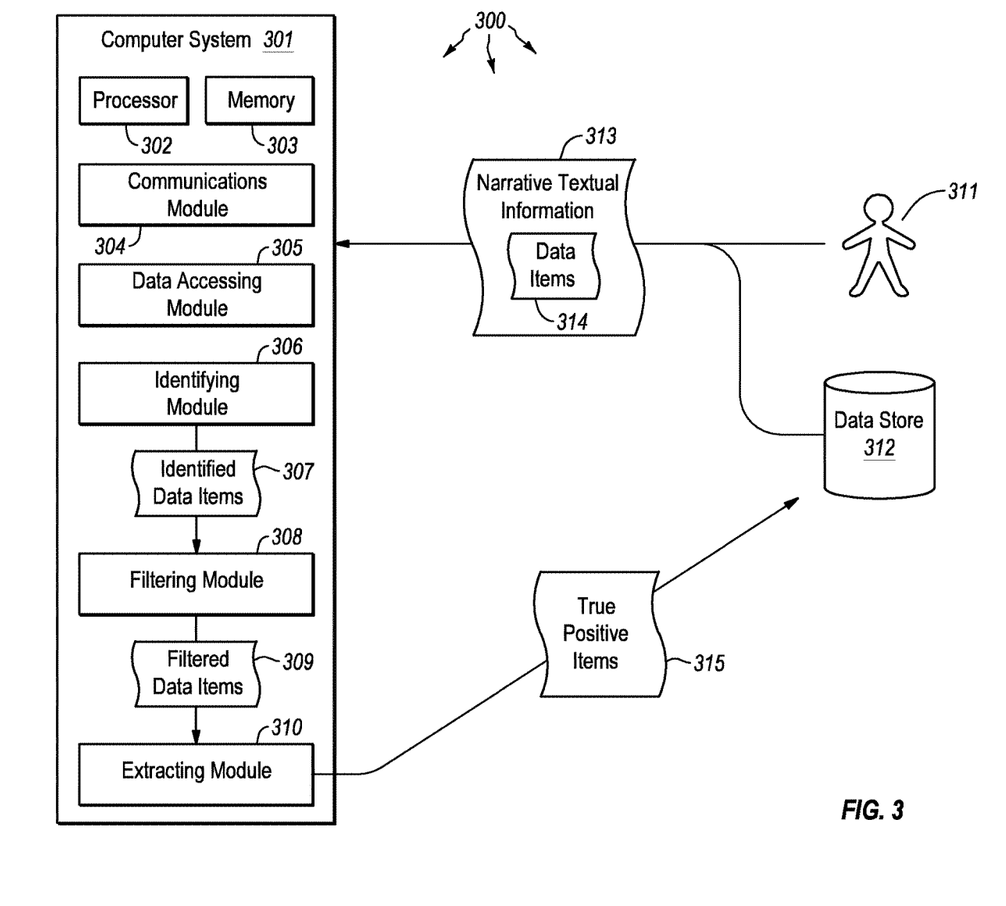
FIG. 3 illustrates another alternative computer architecture in which embodiments described herein may operate including extracting specified data items from narrative text.

FIG. 3 illustrates a computer architecture 300 in which at least one embodiment may be employed. Computer architecture 300 includes computer system 301. Computer system 301 may be any type of local or distributed computer system, including a cloud computing system. The computer system 301 includes modules for performing a variety of different functions. For instance, the communications module 304 may be configured to communicate with other computing systems. The computing module 304 may include any wired or wireless communication means that can receive and/or transmit data to or from other computing systems. The communications module 304 may be configured to interact with databases, mobile computing devices (such as mobile phones or tablets), embedded or other types of computing systems.

Figure 4:
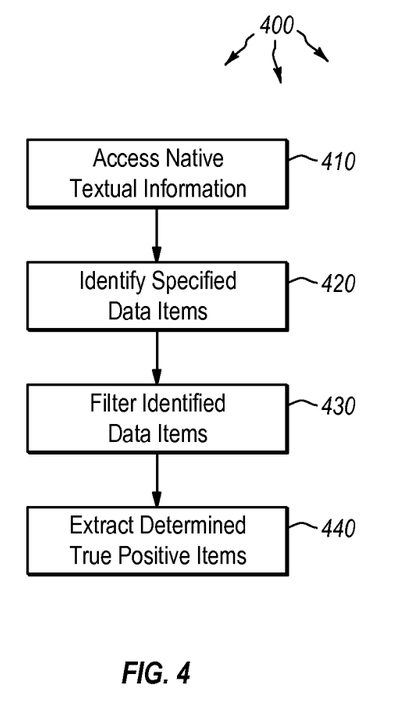
FIG. 4 illustrates an embodiment in which data items are extracted from narrative text.

In one embodiment, the computer system 301 may be implemented to extract specified data items from narrative text. It should be noted that while medical problems and allergies are mentioned herein as examples of specified data, substantially any type of data may be identified and extracted using the methods and systems described herein. Accordingly, data accessing module 305 of computer system 301 may be configured to access one or more portions of narrative textual information 313 (410). The narrative textual information may be taken from substantially any type of document, including a clinical document used by a doctor to keep notes about a patient. The narrative textual information 313 may include various data items 314 that are to be identified and extracted, such as medical problems or allergies such as allergies to medications. Accordingly, while some of the narrative textual information may not be highly relevant to a medical professional, embodiments described herein are designed to find and filter those data items that are or may be relevant to a medical professional. As such, these data items may comprise medical conditions, problems, allergies, sickness patterns, signs, symptoms, diagnoses, treatments, test results, or other data. In some cases, a user 111 (such as a doctor or medical staff member) may be able to specify which terms or types of terms are to be identified by identifying module 306 as specified data items.

In some cases, a clinical document that is to be searched for specified terms is annotated with one or more portions of annotation information. The annotations may have been added manually, or automatically by a software program. In cases where the annotations have been added automatically, an annotations schema may be used to annotate the clinical document. The annotations schema may include a list of specified data items (or data types) that are to be annotated. The annotations schema used to annotate the clinical document may include any of the following: medical problems, allergies (including medication allergies), or any other type of data, including data modifiers that modify the subject, temporality, negation and certainty of a medical condition.

Continuing this embodiment, the identifying module 306 of computer system 301 may then identify specified data items 307 in the narrative textual information 313 that are to be extracted from the narrative textual information (420). The identifying may include any or all of the following: performing a dictionary-based search, performing a pattern-based search and implementing machine learning to identify the data items that are to be extracted. In some cases, the dictionary search may implement performance parameters that maximize identification of specified data items 307 at the expense of falsely identifying non-specified data items. Similarly, the pattern-based search may implement sensitive patterns that maximize identification of specified data items at the expense of falsely identifying non-specified data items. Thus, identifying a data item may be performed with high sensitivity to identify every possible specified data type, even if the result is having multiple false positives. The identifying step may also use context around each specified data item in order to properly identify the item. For instance, the identifying module 306 may use context such as words next to and following the specified data item, as well as the structure of the document, to identify items of interest.

Computer system 301 may then filter the identified data items to remove false positive identifications (430). The false positive filtering, performed by filtering module 308, may include classifying the identified data items 307 as specified data items, so that classified data items are identified as true positive items 315 that are to be extracted from the narrative textual information. The extracting module 310 of computer system 301 may then extract, from the narrative textual information 313, those filtered data items 309 that were classified as being true positive items 315 (440). These specified data items may be extracted in real-time as the data items are being filtered from the identified data items 307. The determined true positive items 315 (such as a determined medical condition or allergy) are transferred to a user such as user 111 or may be transferred to a data store 112. The true positive items may be stored in a local or distributed data store, and may be accessible to the user 111 in a variety of forms. Because the true positive items are identified, filtered and extracted items, it is much more likely that the true positive items 315 will be useful to medical professional or staff member. Accordingly, methods, systems and computer program products are provided in which specified data items are identified and extracted from narrative text.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

We claim:

1. A computer system comprising the following:
one or more processors; and
one or more computer-readable storage media having stored thereon computer-executable instructions that are executable by the one or more processors to configure the computer system to provide an enriched electronic health record (EHR) system that performs characterization of clinical narrative text by facilitating a dual step approach for identifying medical data items from within the clinical narrative text, the dual step approach including (1) a first process of overidentifying medical data items from within the clinical narrative text by not considering false positive information and (2) a second process of determining whether each medical data item included in the overidentified medical data items was falsely or accurately characterized, the computer-executable instructions causing the computer system to:
access one or more portions of the clinical narrative text which is determined to be associated with at least one medical patient, the clinical narrative text including one or more data items that are to be identified and extracted;
as a part of the first process of overidentifying medical data items from within the clinical narrative text by not considering false positive information, generate an overly inclusive collection that includes clinical narrative text portions that are identified as satisfying a minimum interest requirement such that the overly inclusive collection is generated without regard to including false positives in the overly inclusive collection, wherein the one or more data items are included in the overly inclusive collection, and wherein identifying the one or more data items that are included in the overly inclusive collection includes (1) performing a dictionary-based search or a pattern-based search on the one or more data items and (2) instantiating one or more machine learning programs to refine and enrich search results obtained from the dictionary-based or pattern-based searches;
as a part of the second process of determining whether each medical data item included in the overidentified medical data items was falsely or accurately characterized, apply a filter to the overly inclusive collection to remove any false positive items such that only the one or more data items, which are determined to be true positive items, remain, wherein the second process is independent and distinct from the first process;
extract, from the clinical narrative text, the one or more data items, which were classified as being the true positive items;
infer, based on the true positive items, one or more potential medical problems or allergies associated with the at least one medical patient, wherein at least one of the inferred one or more potential medical problems or allergies had not been previously detected, the at least one of the inferred one or more potential medical problems or allergies that was not previously detected constituting a previously undetected data item;
generate a visualized clinical narrative that includes the inferred one or more potential medical problems or allergies that were inferred based on the true positive items, including the previously undetected data item; and present the visualized clinical narrative on a display device to a medical professional, thereby notifying the medical professional in real time of the previously undetected data item, further increasing a likelihood that a proper diagnosis and prescription will be administered to the at least one medical patient, wherein the enriched EHR system provides an extended output to the medical professional who is viewing the visualized clinical narrative by highlighting conflicts and/or errors associated with medical data items identified by the enriched EHR system, by indicating how the medical data items, which describe the visualized clinical narrative, were extracted, and by noting from what source the medical data items describing the clinical narrative were extracted.

2. The computer system of claim 1, wherein the one or more data items comprise at least one of signs, symptoms, diagnoses, treatments, or test results.

3. The computer system of claim 1, wherein the clinical narrative text is included in a clinical document.

4. The computer system of claim 3, wherein the clinical document is annotated with one or more portions of annotation information.

5. The computer system of claim 4, wherein an annotations schema is used to annotate the clinical document, the annotations schema comprising a list of information that is to be annotated.

6. The computer system of claim 5, wherein the annotations schema used to annotate the clinical document includes at least one of the following: signs, symptoms, diagnoses, treatments, or test results and modifiers including subject, temporality, negation and certainty.

7. The computer system of claim 1, wherein the one or more data items are extracted in real-time.

8. The computer system of claim 1, wherein the dictionary-based search implements performance parameters that maximize identification of the one or more data items.

9. The computer system of claim 1, wherein the pattern-based search implements sensitive patterns that maximize identification of the one or more data items.

10. One or more hardware storage devices having stored thereon computer-executable instructions that are executable by one or more processors of a computer system to configure the computer system to provide an enriched electronic health record (EHR) system that performs characterization of clinical narrative text by facilitating a dual step approach for identifying medical data items from within the clinical narrative text, the dual step approach including (1) a first process of overidentifying medical data items from within the clinical narrative text by not considering false positive information and (2) a second process of determining whether each medical data item included in the overidentified medical data items was falsely or accurately characterized, the computer-executable instructions causing the computer system to:

access one or more portions of the clinical narrative text which is determined to be associated with at least one medical patient, the clinical narrative text including one or more data items that are to be identified and extracted;

as a part of the first process of overidentifying medical data items from within the clinical narrative text by not considering false positive information, generate an overly inclusive collection that includes clinical narrative text portions that are identified as satisfying a minimum interest requirement such that the overly inclusive collection is generated without regard to including false positives in the overly inclusive collection, wherein the one or more data items are included in the overly inclusive collection, and wherein identifying the one or more data items that are included in the overly inclusive collection includes (1) performing a dictionary-based search or a pattern-based search on the one or more data items and (2) instantiating one or more machine learning programs to refine and enrich search results obtained from the dictionary-based or pattern-based searches;

as a part of the second process of determining whether each medical data item included in the overidentified medical data items was falsely or accurately characterized, apply a filter to the overly inclusive collection to remove any false positive items such that only the one or more data items, which are determined to be true positive items, remain, wherein the second process is independent and distinct from the first process;

extract, from the clinical narrative text, the one or more data items, which were classified as being the true positive items;

infer, based on the true positive items, one or more potential medical problems or allergies associated with the at least one medical patient, wherein at least one of the inferred one or more potential medical problems or allergies had not been previously detected, the at least one of the inferred one or more potential medical problems or allergies that was not previously detected constituting a previously undetected data item;

generate a visualized clinical narrative that includes the inferred one or more potential medical problems or allergies that were inferred based on the true positive items, including the previously undetected data item; and present the visualized clinical narrative on a display device to a medical professional, thereby notifying the medical professional in real time of the previously undetected data item, further increasing a likelihood that a proper diagnosis and prescription will be administered to the at least one medical patient, wherein the enriched EHR system provides an extended output to the medical professional who is viewing the visualized clinical narrative by highlighting conflicts and/or errors associated with medical data items identified by the enriched EHR system, by indicating how the medical data items, which describe the visualized clinical narrative, were extracted, and by noting from what source the medical data items describing the clinical narrative were extracted.

11. The one or more hardware storage devices of claim 10, wherein a data item identifying module identifies specified data items using use context around each specified data item.

12. The one or more hardware storage devices of claim 10, wherein the context includes words next to and following the specified data item and the structure of the document.

13. The one or more hardware storage devices of claim 10, wherein a data item identifying module implements one or more performance parameters that maximize identification of specified data items at the expense of falsely identifying non-specified data items.

14. At a computing system comprising a processor and a memory, a computer-implemented method for providing an enriched electronic health record (EHR) system that performs characterization of clinical narrative text by facilitating a dual step approach for identifying medical data items from within the clinical narrative text, the dual step approach including (1) a first process of overidentifying medical data items from within the clinical narrative text by not considering false positive information and (2) a second process of determining whether each medical data item included in the overidentified medical data items was falsely or accurately characterized, the method comprising the following:

accessing one or more portions of the clinical narrative text which is determined to be associated with at least one medical patient, the clinical narrative text including one or more data items that are to be identified and extracted;

as a part of the first process of overidentifying medical data items from within the clinical narrative text by not considering false positive information, generating an overly inclusive collection that includes clinical narrative text portions that are identified as satisfying a minimum interest requirement such that the overly inclusive collection is generated without regard to including false positives in the overly inclusive collection, wherein the one or more data items are included in the overly inclusive collection, wherein identifying the one or more data items that are included in the overly inclusive collection includes (1) performing a dictionary-based search or a pattern-based search on the one or more data items and (2) instantiating one or more machine learning programs to refine and enrich search results obtained from the dictionary-based or pattern-based searches;

as a part of the second process of determining whether each medical data item included in the overidentified medical data items was falsely or accurately characterized, applying a filter to the overly inclusive collection to remove any false positive items such that only the one or more data items, which are determined to be true positive items, remain, wherein the second process is independent and distinct from the first process;

extracting, from the clinical narrative text, the one or more data items, which were classified as being the true positive items;

inferring, based on the true positive items, one or more potential medical problems or allergies associated with the at least one medical patient, wherein at least one of the inferred one or more potential medical problems or allergies had not been previously detected, the at least one of the inferred one or more potential medical problems or allergies that was not previously detected constituting a previously undetected data item;

generating a visualized clinical narrative that includes the inferred one or more potential medical problems or allergies that were inferred based on the true positive items, including the previously undetected data item; and     presenting the visualized clinical narrative on a display device to a medical professional, thereby notifying the medical professional in real time of the previously undetected data item, further increasing a likelihood that a proper diagnosis and prescription will be administered to the at least one medical patient,     wherein the enriched EHR system provides an extended output to the medical professional who is viewing the visualized clinical narrative by highlighting conflicts and/or errors associated with medical data items identified by the enriched EHR system, by indicating how the medical data items, which describe the visualized clinical narrative, were extracted, and by noting from what source the medical data items describing the clinical narrative were extracted.

15. The method of claim 14, wherein the clinical narrative text is included in a clinical document.

16. The method of claim 15, wherein the clinical document is annotated with one or more portions of annotation information.

17. The method of claim 16, wherein an annotations schema is used to annotate the clinical document, the annotations schema comprising a list of information that is to be annotated.

18. The method of claim 17, wherein the annotations schema used to annotate the clinical document includes at least one of the following: signs, symptoms, diagnoses, treatments, or test results and modifiers including subject, temporality, negation and certainty.

19. The method of claim 14, wherein the dictionary-based search implements performance parameters that maximize identification of the one or more data items.

20. The one or more hardware storage devices of claim 10, wherein the specified data items comprise at least one of signs, symptoms, diagnoses, treatments, or test results.

* * * * *